(12) United States Patent
Lindquist

(10) Patent No.: US 7,686,773 B2
(45) Date of Patent: Mar. 30, 2010

(54) INJECTION DISTRACTION DEVICE

(75) Inventor: Sherrill F Lindquist, Niveville, FL (US)

(73) Assignee: Raintree Essix, L.L.C., Metairie, LA (US)

( * ) Notice: Subject to any disclaimer, the term of this patent is extended or adjusted under 35 U.S.C. 154(b) by 1197 days.

(21) Appl. No.: 11/043,674

(22) Filed: Jan. 26, 2005

(65) Prior Publication Data
US 2006/0173386 A1 Aug. 3, 2006

(51) Int. Cl.
*A61H 1/00* (2006.01)
(52) U.S. Cl. ................ 601/2; 601/73; 601/46; 601/67; 601/69; 433/86
(58) Field of Classification Search .............. 601/2, 601/73, 46, 67, 69, 80; 433/86, 118, 119
See application file for complete search history.

(56) References Cited

U.S. PATENT DOCUMENTS

| | | | |
|---|---|---|---|
| 2,183,690 A * | 12/1939 | Ostrom | ........................ 433/122 |
| 3,620,209 A | 11/1971 | Kravitz | |
| 4,608,019 A | 8/1986 | Kumabe et al. | |
| 5,437,606 A | 8/1995 | Tsukamoto | |
| 5,639,238 A | 6/1997 | Fishburne, Jr. | |
| 5,873,844 A * | 2/1999 | Campero et al. | ............... 601/2 |
| 6,231,531 B1 | 5/2001 | Lum et al. | |
| 2006/0135892 A1* | 6/2006 | Nan | ............................ 601/72 |

* cited by examiner

*Primary Examiner*—Nicholas D Lucchesi
*Assistant Examiner*—Quynh-Nhu H Vu
(74) *Attorney, Agent, or Firm*—Joseph T Regard, Ltd plc

(57) ABSTRACT

A system for mitigating pain in a patient associated with needle penetration in the administration of medication, and in particular to a vibratory device configured to be utilized with a variety of existing hand-held intra-oral dental drills or like devices. The preferred embodiment of the present invention teaches a disposable or non-disposable vibratory tip formed to engage an off-the-shelf intra-oral dental drill, the vibratory tip utilizing an off-axis weight associated with a shaft drive engaging the dental drill, to provide a vibratory sensation to an application tip, the application tip configured to engage an area of a patient's mouth targeted for the subsequent needled administration of local anesthetic, or other medication. In use, the application tip is applied to the patient, the dental drill is engaged to rotate the shaft drive of the vibratory tip, vibrating same for period of time, so as to decrease the sensation of pain associated with the subsequent needle penetration.

10 Claims, 3 Drawing Sheets

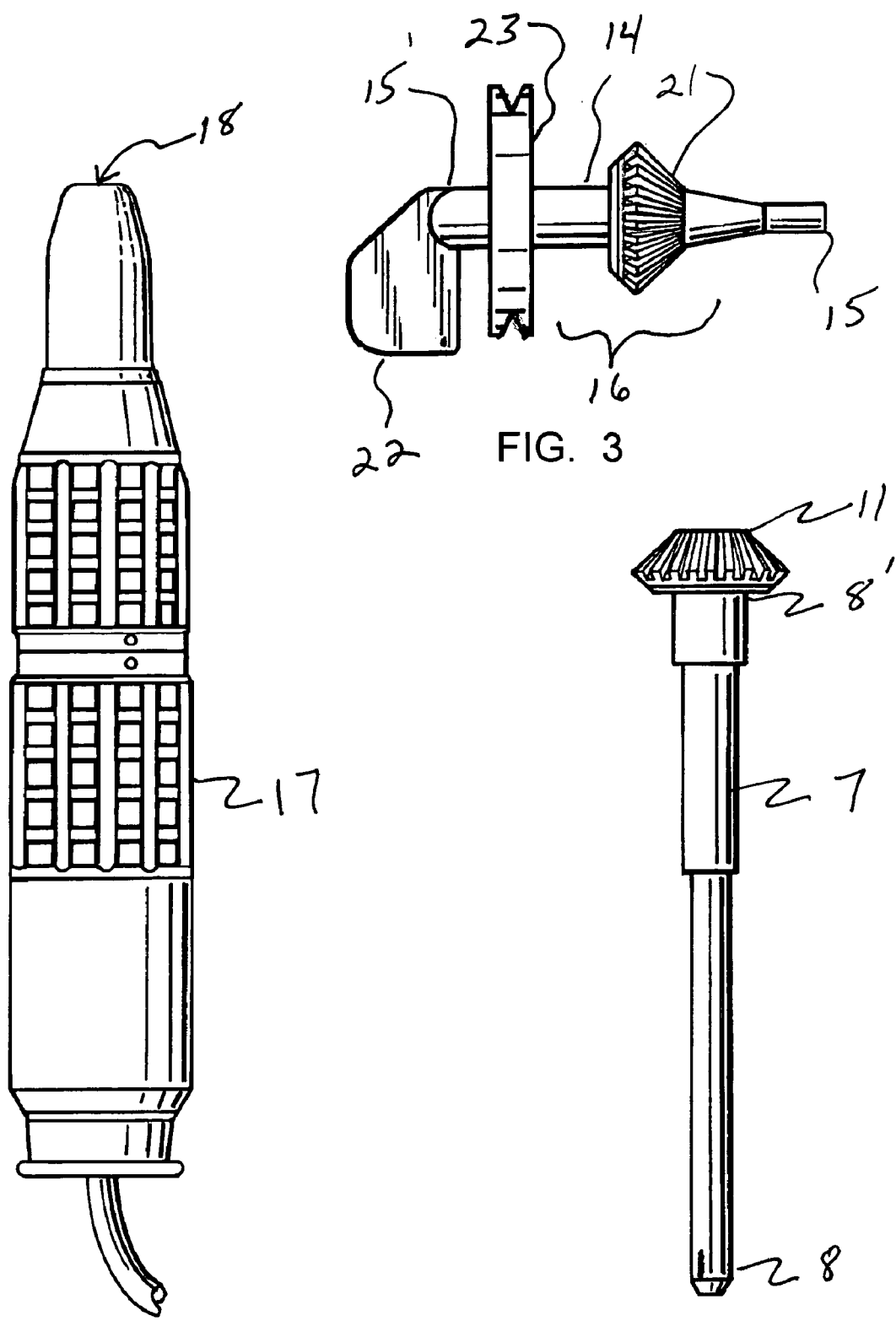

INJECTION DISTRACTION DEVICE

TECHNICAL FIELD OF THE INVENTION

The present invention relates to systems for mitigating pain in a patient associated with an injection associated with the administration of medication, and in particular to a vibratory device configured to be connected to and utilized with a variety of existing hand-held intra-oral dental drills or like devices for numbing the target area prior to injection.

The preferred embodiment of the present invention teaches a disposable or non-disposable vibratory tip piece formed to engage an off-the-shelf dental hand piece, the vibratory tip utilizing an off-axis weight associated with a shaft drive for engaging the dental hand piece, the hand piece rotating the off-axis weight to provide a vibratory sensation to an application tip, the application tip configured to engage an area of a patient's mouth targeted for the subsequent needled administration of local anesthetic, or other medication.

In use, the application tip is applied to the patient, the dental drill is engaged to rotate the shaft drive of the vibratory tip, vibrating the application tip for a period of time, so as to numb the target area to decrease the sensation of pain associated with the subsequent needle penetration.

BACKGROUND OF THE INVENTION

Present conventional dental practice in the United States often involves the application of a viscous solution containing a topical anesthetic such as Benzocaine or the like to intra-oral soft tissues, to numb the target area prior to the needled insertion of a local anesthetic.

The dentist or other clinician applies the topical anesthetic with a cotton swab for 1-2 minutes to the soft tissue area where the dental injection will be inserted. The topical anesthetic deadens the perception of pain in the area where it was introduced.

Unfortunately, the anesthetic also may be spread by the patients tongue, resulting in an unpleasant taste and loss of sensation/control of the tongue and inadvertent numbing of other areas of the mouth; further, the anesthetic may be swallowed. In addition, the topical anesthetic takes time to work, and may not always be effective in sufficiently deadening the pain.

There therefore exists a need in the dental area for a means for deadening the sensation of a needle being introduced into the intra-oral tissues of a patient which does not require medication, which may be applied quickly and effectively, and in a safe, sterile and inexpensive manner.

GENERAL SUMMARY DISCUSSION OF THE INVENTION

Unlike the prior art, the present invention provides a system for numbing a target area on a patient particularly suitable for intra-oral use which requires no anesthetic, in a device which is inexpensive to procure and use, and is safe, sanitary, and effective in operation.

The present invention relates to the mitigation or elimination of intra-oral pain felt by a dental patient when receiving an intra-oral dental injection from a dentist or other licensed clinician, in order to anesthetize a particular intra-oral anatomical structure.

This mitigation or elimination of intra-oral pain is accomplished by the dentist or other licensed clinician by attaching a disposable or non-disposable piece of dental equipment (the vibrating tip) to an existing slow speed or variable speed dental hand piece and motor.

The application tip of the device of the present invention produces a vibration that, when held against the intra-oral soft tissue, produces a numbing sensation which, in turn, mitigates or eliminates the pain associated with a dental injection.

The Melzack and Wall gate control theory of pain (1965) offers a possible explanation as to how the mitigation or elimination of pain is caused by vibrating the tissue. Stimulation of larger diameter nerves (A fibers), which transmit the sensations of touch, pressure, and temperature are believed to block the transmission of smaller diameter nerves (A-delta and C-fibers), which carry sensations of pain.

This blockage, or closed gate, prevents the pain sensation from reaching the brain, where the sensation is perceived as pain.

In the present invention, the vibrating tip possibly functions as a deadening means by heavily stimulating the larger diameter A fibers, and consequently temporarily affecting the conduction of the smaller diameter A-delta and C-fibers.

An exemplary method of use of the present invention, utilizing the preferred device which will be discussed in greater detail infra, involves the following steps:

1) attaching the disposable or non-disposable vibrating tip device of the present invention to a slow or variable speed dental hand piece;

2) positioning the hand piece so that the attached vibrating tip is held against the intra-oral soft tissue (the target area) where the dental injection will be made;

3) initiating the rotation of the hand piece so as to rotate the drive shaft of the vibrating tip, driving the vibration means (for example, and off-balance weight), providing a vibrating tip;

4) holding the vibrating tip for a desired period of time to target area; and 5) removing the vibrating tip from the intra-oral soft tissue comprising the target area, and proceeding with the dental injection.

The present procedure, when utilized as a replacement for the prior art method of utilizing local topical anesthetic, has been found to provide equally satisfactory or improved results, realizes the reduction of required dentist time, and provides a procedure that tends to make the administration of dental injections a more positive experience.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 3 is a side view of the lateral drive shaft of FIG. 1, having an off-center weight applied thereto.

FIG. 4 is a side view of the longitudinal drive shaft of the invention of FIG. 1.

FIG. 5 is a side view of an exemplary hand-held rotary drive unit.

DETAILED DISCUSSION OF THE INVENTION

Figures 1, 2:
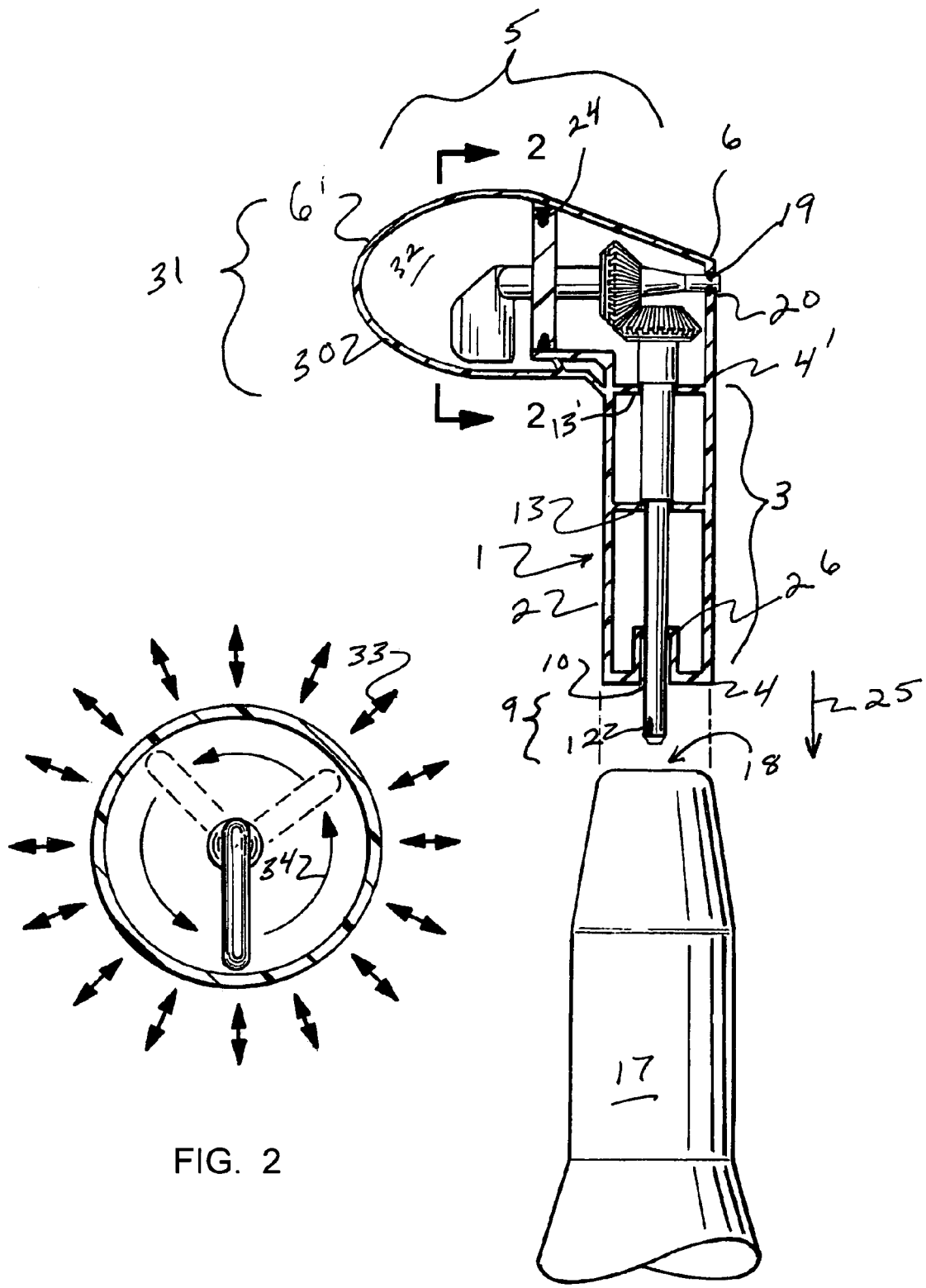
FIG. 1 is a side, partially cut-away view of the preferred exemplary embodiment of the present invention positioned for engagement to an exemplary off-the-shelf drive/hand piece.
FIG. 2 is a top, cut-away view of the off-center weight of the invention of FIG. 1 rotating via the driveshaft, causing vibration of the tip.

Referring to FIGS. 1-5, the preferred embodiment of the present invention comprises a device 1 in the form of a vibrating application tip configured to engage a low speed or variable low speed dental hand piece in similar manner as existing dental prophylaxis cup angle (also referred to as a "prophy"). An example of a compatible hand piece used in the present system comprises, for example, the Midwest brand straight attachment 17, which fits upon a low speed motor, to provide a low speed dental hand piece.

It is iterated that there are several other manufacturers that provide low-speed dental hand pieces which would be compatible with the device 1 of the present invention, and other exemplary brands and models are listed infra, although said listing is not intended to be comprehensive or limiting.

The device 1 comprises an outer body casing 2 having a cavity there through, the casing comprising a longitudinal portion 3 having first 4 and second 4' ends, and a lateral portion 5 having first 6 and second ends 6', the lateral portion engaging the longitudinal portion at ends 4', 6', respectively.

Situated within the longitudinal portion 3 of the casing is a first drive shaft 7 having first 8 and second 8' ends, the first end 8 of the shaft 7 emanating 10 from the first end 4 of the longitudinal portion of the body to provide an exposed shank 9, the shank having a notch 12 for engaging 25 a chuck 18 situated at the end of the hand piece 17.

The second end 8' of the first drive shaft 7 has mounted thereon a 90 degree shaft gear 11. The first drive shaft 7 is rotatably supported within the longitudinal portion 3 of the casing via first 13 and second 13' support points.

Situated within the lateral portion 5 of the outer body casing is a second, laterally situated drive shaft 14 having first 15 and second 15' ends, and a medial portion 16 there between.

As shown, the first end 15 of the second shaft 14 engages the outer body casing at aperture 20, a gear nub 19 formed therein to rotatingly engage the end of the shaft. The first end of the second drive shaft is situated in the vicinity of the second end 8' of the first drive shaft 7, the second drive shaft having mounted thereon a 90 degree shaft gear 21 engaging the 90 degree shaft gear 11 mounted to the first drive shaft 7.

An off-center weight 22 is provided at the second end 15' of the second, lateral drive shaft 14, while a collar 23 is situated along shaft 14 between the off-center weight 22 and shaft gear 21, the collar 23 engaging a nub 24 where the periphery of the collar 23 rotatingly engages 25 the casing to rotatingly support the second drive shaft 14 in operation.

A shell/cover 30 is formed about the off-center weight 22 to provide a cavity 32 sufficient in size to allow the unimpeded rotation of the off-center weight therein, the outer surface of the shell/cover portion forming an application surface 31, the above design thereby providing a contra-angle vibrating tip which allows the dentist to have greater access to various locations in the oral cavity.

In use, the exposed shank 9 is placed into the chuck 18 of the hand piece 17, engaging same. A mechanical coupling, such as a notch 26 or alternatively a twist lock, as is commonly used in plastic fabrications, can also be provided to engage the first end 4 of the longitudinal portion 3 of the device to an engaging member formed at the tip of the hand piece.

The hand piece is then engaged, the chuck rotating the first drive shaft 8, which engages and rotates the second, lateral drive shaft 14, rotating 34 the off-center weight 22, causing a rapid circular motion resulting in a vibration 33, which vibration is transferred via the casing 2 to the application surface 31.

In treating a patient, the a motor drives the hand piece, which in turn drives the present device 1, rotating the off-center weight at a revolutions per minute (RPM) range of, for example, 1 to 40,000 RPMs, with a preferred RPM range of 500 to 6,000.

Figure 6:
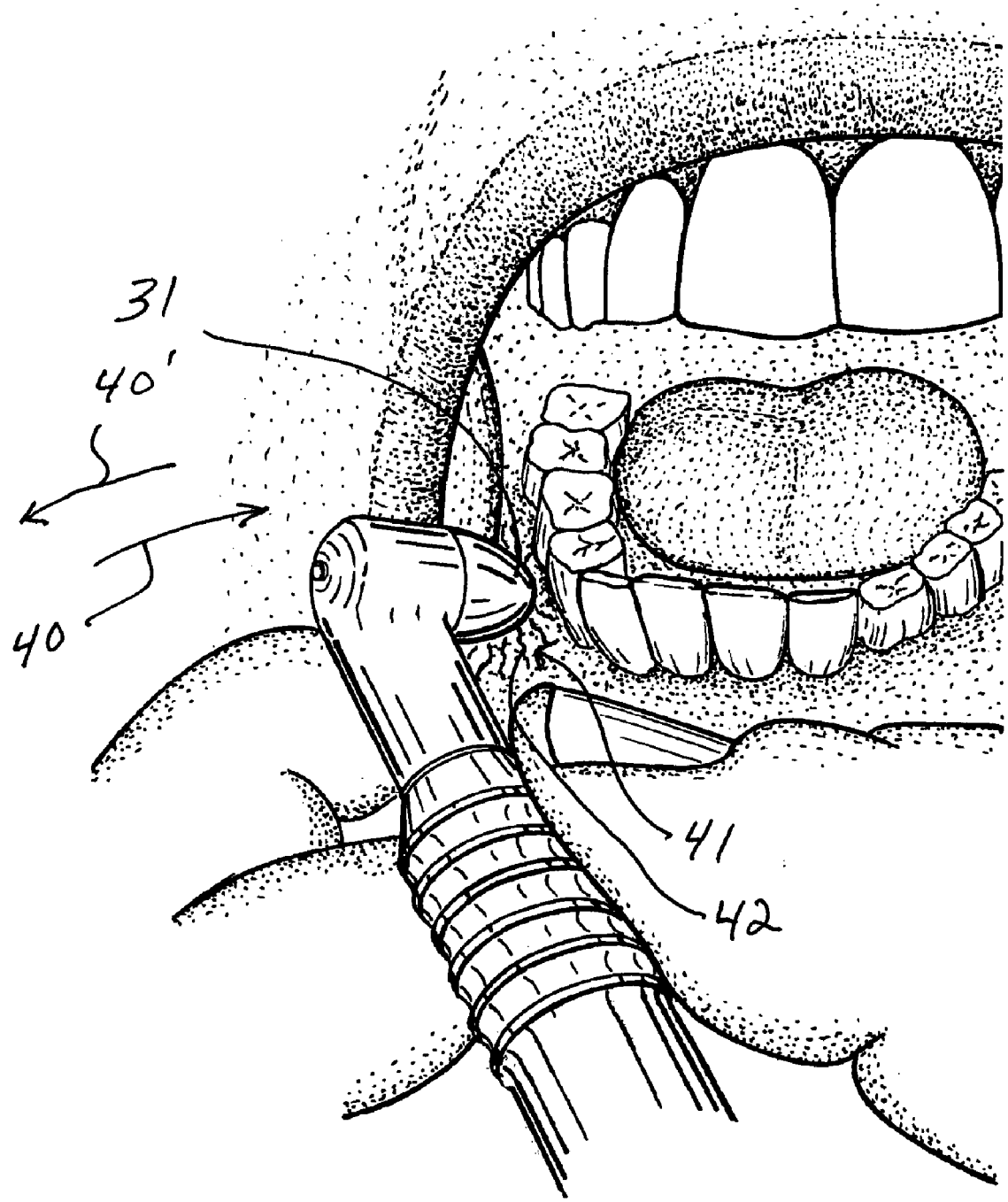
FIG. 6 is an isometric view of the vibrating tip of the invention of FIG. 1 as applied intra-orally to a patient.

Referring to FIG. 6, the vibrating 42 application surface 31 is then applied to the target area 41 of the patient (the area where the injection or other procedure is to be made) for a predetermined period of time, for example, 15-30 seconds, although the application time could vary from 1-60+ seconds, depending upon the patient's perception of pain, the severity of the procedure, etc. After the period of time has lapsed, the application surface is removed 40' from the area.

The care giver then may carefully apply the injection via needle, or other procedure to the application area, while judging the patient's perception of pain. If it is determined the patient still feels pain at an unacceptable level during application of the needle, the procedure utilizing the vibrating application tip to the target area may be repeated, until adequate numbing of the intra-oral soft tissue and adjacent area is determined.

The present device is designed to be universally utilized with a variety of low speed dental hand pieces which accept dental prophy angles.

In the present, preferred embodiment, the motor driving the hand piece is an air motor, and has a variably adjustable RPM of 30 to 30,000 via a standard dental foot pedal, which alters the air pressure running through the low-speed dental hand piece, although the device of the present invention is believed to have an optimal operational range of about 500 to 6,000 RPM. Because the system relies upon pneumatic air, there is thus no necessity for batteries or electrical outlets in the immediate area.

The design of the present device allows it to be manufactured at very low cost, believed less than $1.00 (one dollar U.S.) per unit. The device could be disposable and packaged in sterilized fashion so that no autoclaving by the care giver is ever necessary; the item is simply discarded after use on a patient.

Exemplary off-the-shelf low speed dental hand pieces which would be compatible include, for example:
1) KaVo Intramatic brand low speed system.
2) Henry Schein Maxima brand low speed hand piece system.
3) Star Dental Titan brand low speed hand piece system.
4) Midwest brand low-speed hand piece systems.
5) Micro Motors, Inc. PHP brand series prophy hand pieces.

All of the above hand piece systems are operated by air driven motors and operate within an RPM range of 0-30,000. While virtually all dentists use air driven motors for their low-speed hand pieces, electric motors are starting to emerge in the marketplace, and would not be incompatible with the present system.

A summary of the method of the present invention, could comprise, for example, the steps of:

The method of preparing an intra-oral target area on a patent for treatment, comprising the steps of:
  a) providing a device having:
    a first drive shaft having first and second ends said second end formed to rotate an off-center weight;
    a cover enveloping said off-center weight, at least part of said cover comprising an application surface;
  b) applying said first end of said first drive shaft to a chuck associated with a hand piece;

c) applying said application surface to an intra-oral target area on a patient;

d) initiating a motor to rotate said chuck and first drive shaft, rotating said off center-weight to vibrate said application surface, so as to provide a vibrating application surface, e) utilizing said vibrating application surface to vibrate said target area on said patient for a pre-determined period of time, providing a treated target area;

f) disengaging said motor, ceasing rotation of said off-center weight, ceasing vibration of said application surface;

g) removing said application surface from said target area; and h) treating the patient at said treated target area.

A listing of the elements of the invention cited above follows:

ELEMENT DESCRIPTION 1 device
2 outer body casing
3 longitudinal portions
4,' first end, second end
5 lateral portion
6,' first, second ends
7 first, longitudinal drive shaft
8,' first, second ends
9 shank
10 emanating
11 90 degree shaft gear
12 notch in base to engage hand piece
13,' support points for longitudinal drive shaft
14 second, lateral drive shaft
15 first, second ends
16 medial portion
17 hand piece
18 chuck
19 gear nub at fist end of lateral shaft
20 aperture in cover for first end of lateral shaft
21 90 degree shaft gear engaging lateral drive shaft gear
22 off-center weight
23 collar engaging casing
24 nub
25 engage
26 notch
30 shell/cover portion
31 application surface
32 cavity
33 vibration
34 rotation
40,' applied, removed
41 target area
42 vibrating The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. The method of utilizing a dental hand piece for preparing an intra-oral target area on a patient for treatment, comprising the steps of:

a) providing an adapter formed to fit to a dental hand piece in the form of a device having:

a first drive shaft having first and second ends, a second drive shaft having first and second ends, said first end of said second drive shaft formed to engage said second end of said first drive shaft at an angle, said second end of said second drive shaft formed to engage and rotate an off-center weight;

an outer body casing enveloping said off-center weight, at least part of said outer body casing comprising an application surface;

said second drive shaft having affixed to and laterally enamanting therefrom a collar having an outer diameter configured to rotatingly engage said outer body casing via a nub;

b) applying said first end of said first drive shaft to a chuck associated with a dental hand piece;

c) applying said application surface to an intra-oral target area on a patient;

d) initiating a motor associated with said dental hand piece to rotate said chuck and first drive shaft, rotating said second drive shaft so as to rotate said off-center weight to provide vibration to said second drive shaft; while using said collar to transfer said vibration from said second shaft to said outer housing via said nub, so as to provide a vibrating application surface;

e) utilizing said vibrating application surface to vibrate said target area on said patient for a pre-determined period of time, providing a treated target area;

f) disengaging said motor, ceasing rotation of said off-center weight, ceasing vibration of said application surface;

g) removing said application surface from said target area; and h) treating the patient at said treated target area.

2. The method of claim 1, wherein in claim "d" said off-center weight is rotated at a speed of between 500 to 6,000 revolutions per minute.

3. The method of claim 2, wherein in claim "e", said target area is vibrated via said vibrating application surface for a predetermined period of time comprising between one to sixty seconds.

4. The method of claim 3, wherein in step "h" said treatment comprises an injection utilizing a needle.

5. The method of claim 4, wherein there further comprises after step "g" the additional step "g1" of testing said treated target area to determine sufficiency of treatment, and wherein, if it is determined that said treatment is insufficient, repeating steps "c"-"g".

6. The method of claim 1, where in step "a" there is provided the added step "a2" of providing pinion gears to said first and second drive shafts at their respective engagement points to facilitate rotational communication between said first and second drive shafts.

7. The device of claim 1 wherein in step "a" said second drive shaft is situated at an angle relative to said first end of said first drive shaft, said housing has an exterior wall, and said exterior wall of said housing engages and rotatingly supports said first ends of said first and second drive shafts, while in step "d" the step of engaging said motor to rotate said first drive shaft further includes the step of utilizing said first drive shaft to engage and rotate said second drive shaft, rotating said off center weight and providing vibration to said application surface.

8. The method of claim 7, wherein in step application "b" surface is situated in spaced relationship laterally from said dental hand piece, and wherein in step "c" there is further provided the step of utilizing said application surface to treat the gums of said patient.

9. The device of claim 1, wherein in step "b" there is further provided the step of providing a collar emanating about said second drive shaft, said collar having an outer diameter configured to rotatingly engage said outer body casing, said collar formed to support and stabilize said second drive shaft, step "d" further comprising the step of utilizing said collar to support and stabilize said second drive shaft as said off center weight is rotated.

10. The method of claim 9, wherein step "b" further comprises the step of providing a nub associated with said outer diameter of said collar, said nub formed to rotatingly engage said collar to said outer body casing and wherein step "b" further comprises the step of utilizing said nub and said outer body casing to support said collar as said off center weight is rotated, while transferring vibratory forces from said rotating off center weight to said application surface.

\* \* \* \* \*